United States Patent [19]

Rosenberg

[11] Patent Number: 4,600,402
[45] Date of Patent: Jul. 15, 1986

[54] CATHETER WITH LOCKING DEVICE

[75] Inventor: Helmut W. G. Rosenberg, McHenry, Ill.

[73] Assignee: The Kendall Company, Boston, Mass.

[21] Appl. No.: 683,053

[22] Filed: Dec. 18, 1984

[51] Int. Cl.$^4$ ............................................. A61M 25/00
[52] U.S. Cl. ...................................... 604/96; 604/283
[58] Field of Search ................................. 604/96–103, 604/283

[56] References Cited

U.S. PATENT DOCUMENTS

| 3,112,748 | 12/1963 | Colburn | 604/100 |
| 3,805,794 | 4/1974 | Schlesinger | 604/103 X |
| 4,431,426 | 2/1984 | Groshong et al. | 604/283 X |
| 4,511,163 | 4/1985 | Harris et al. | 604/283 X |

Primary Examiner—Dalton L. Truluck
Attorney, Agent, or Firm—Powell L. Sprunger

[57] ABSTRACT

A catheter comprising, a first distal shaft section having a first distal drainage lumen extending therethrough, and a first inflation lumen extending through a wall of the first shaft section. The catheter has an elastic sleeve bonded to a distal portion of the first shaft section in circumferential zones defining a cavity beneath the sleeve communicating with the first inflation lumen. The catheter has a proximal portion comprising a second proximal shaft section having a second drainage lumen extending therethrough, a hollow connector defining a continuation of the second drainage lumen, a side arm having a valve, and a second inflation lumen extending through the side arm from the valve and through the second shaft section to a distal end of the proximal portion. The catheter has a device for locking the first shaft section to the proximal portion while establishing communication between the first and second drainage lumens and between the first and second inflation lumens.

3 Claims, 8 Drawing Figures

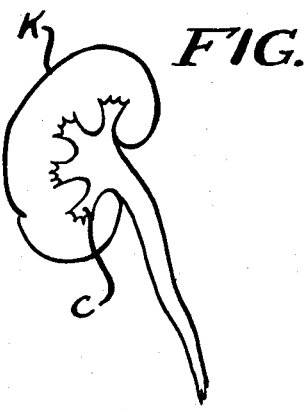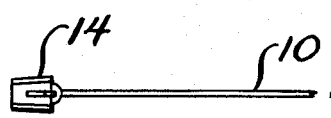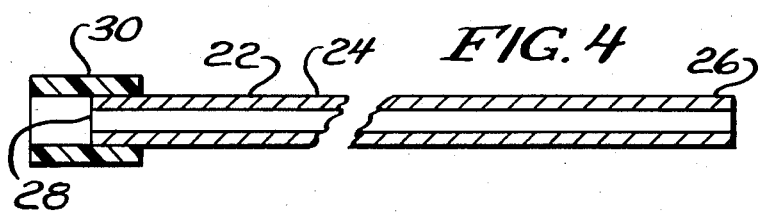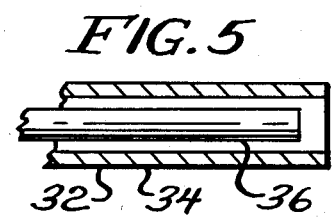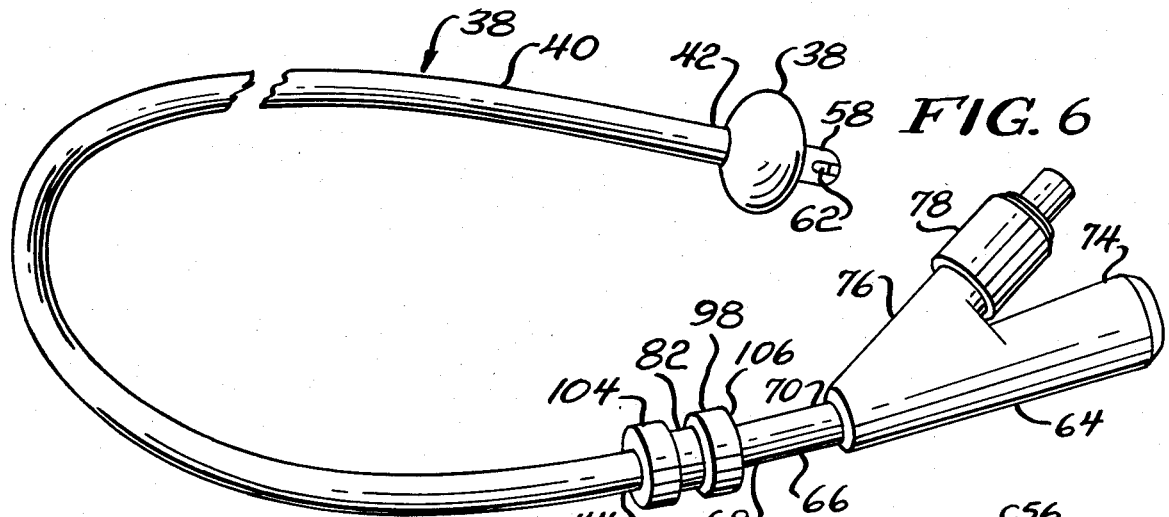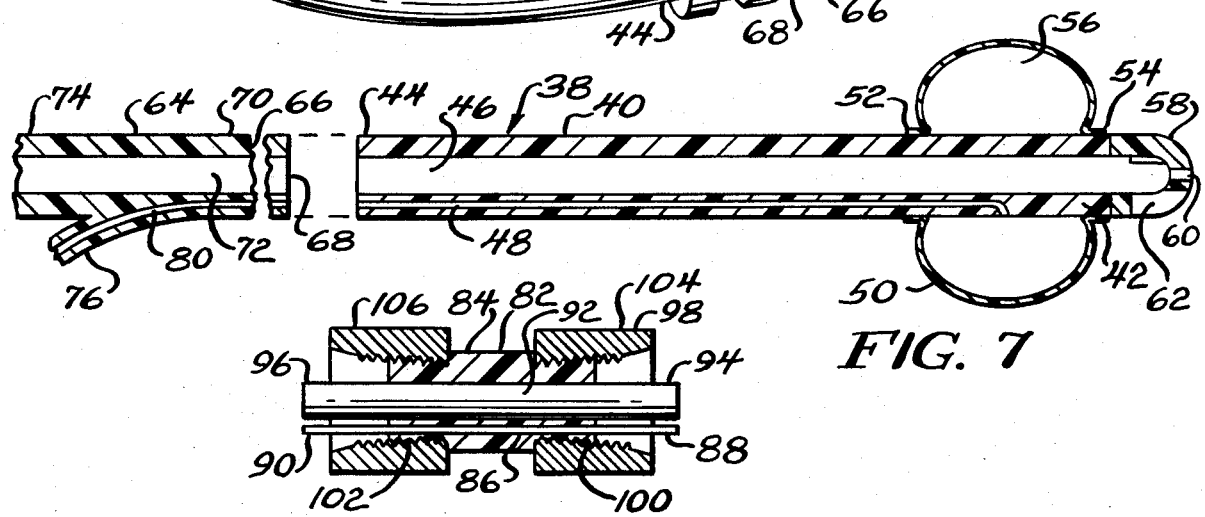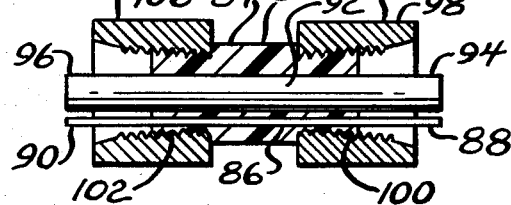

CATHETER WITH LOCKING DEVICE

BACKGROUND OF THE INVENTION

The present invention relates to catheters.

When the ureter or kidney of a patient is obstructed by a stone, it is necessary to stabilize the kidney through drainage because an increase of pressure in the kidney could result in loss of the kidney. Such a procedure is called a nephrostomy procedure. First, a small gauge hollow needle is passed under radiologic vision until a tip of the needle is located in the renal calyces to obtain access to the kidney chamber. With the needle in place, a flexible elongated guide wire is passed through the needle, and the needle is removed with the guide wire in place to establish a path to the kidney. Next, a plurality of dilators are inserted over the guide wire in order to increase the size of the path to the kidney, and the dilators are then removed. In the past, a catheter is then placed over the guide wire, with the catheter having a pig tail which is located in the kidney. Although nephrostomy has been completed in this manner, it is desired to improve the procedure.

SUMMARY OF THE INVENTION

A principal feature of the present invention is the provision of an improved catheter for performing a nephrostomy procedure.

The catheter of the invention comprises, a first distal shaft section having a first distal drainage lumen extending therethrough, and a first inflation lumen extending through a wall of the first shaft section. The catheter has an elastic sleeve bonded to a distal portion of the first shaft section in circumferential zones defining a cavity beneath the sleeve communicating with the first inflation lumen. The catheter has a proximal portion comprising a second proximal shaft section having a second drainage lumen extending therethrough, a hollow connector defining a continuation of the second drainage lumen, a side arm having a valve, and a second inflation lumen extending through the side arm from the valve and through the second shaft section to a distal end of the proximal portion.

A feature of the present invention is a provision of means for locking the first shaft section to the proximal portion.

Another feature of the invention is that the locking means establishes communication between the first and second drainage lumens and between the first and second inflation lumens.

Yet another feature of the invention is that the sleeve may be inflated through the inflation lumens when the locking means connects the first shaft section to the proximal portion.

Still another feature of the invention is that liquid may drain through the first and second drainage lumens when the locking means secures the first shaft section to the proximal portion.

A further feature of the invention is that the locking means may release the proximal portion from the first shaft section in order to permit passage of the sheath of a scope over the first shaft section.

Further features will become more fully apparent in the following description of the embodiments of this invention and from the appended claims.

DESCRIPTION OF THE DRAWINGS

In the drawings:

FIG. 1 is a diagrammatic view of a kidney of a patient;

FIG. 2 is a fragmentary elevational view of a needle for use in a nephrostomy procedure;

FIG. 3 is a fragmentary elevational view of a guide wire for use in the procedure;

FIG. 4 is a fragmentary elevational view of a stylet for use in the procedure;

FIG. 5 is a fragmentary elevational view of a scope for use in the procedure;

FIG. 6 is a perspective view of a catheter of the present invention;

FIG. 7 is a fragmentary sectional view of a catheter of FIG. 6; and

FIG. 8 is a sectional view of a locking device for the catheter of FIG. 6.

DESCRIPTION OF THE PREFERRED EMBODIMENTS

Referring now to FIG. 1, there is shown a kidney K of a patient having a renal calyces C forming a cavity in the kidney K. Referring to FIG. 2, there is shown a hollow needle 10 having a distal sharp tip 12, and a proximal hub 14. Referring to FIG. 3, there is shown a guide wire 16 of flexible material having a distal end 18, and a proximal end 20. Referring to FIG. 4, there is shown a stylet 22 having an elongated hollow rigid tube 24. The tube 24 has a distal end 26, and a proximal end 28. The stylet 22 has a flexible tubular section 30 of plastic material frictionally received on the proximal end 28 of the tube 24. Referring to FIG. 4, there is shown a scope 32 having a hollow outer elongated sheath 34, and an inner optic telescope 36 removably received in the sheath 34.

The catheter 38 of the present invention is illustrated in FIGS. 6 and 7. The catheter 38 has a first distal shaft section 40 having a distal end 42, a proximal end 44, and a first distal drainage lumen 46 extending through the first shaft section 40. The first shaft section 40 has a first inflation lumen 48 extending through a wall of the first shaft section 40. The first shaft section 40 has an elastic sleeve 50 bonded to a distal portion of the first shaft section 40 in circumferential zones 52 and 54, such that the sleeve 50 defines a cavity 56 beneath the sleeve 50 communicating with the first inflation lumen 48.

The first shaft section 40 has a formed tip 58 bonded to the distal end 42 of the first shaft section 40. The tip 58 has a distal opening 60 extending through the tip 58 and communicating with the first drainage lumen 46. The tip 58 also has a plurality of drainage eyes 62 located proximal the opening 60 and extending through the tip 58 and communicating with the first drainage lumen 46.

The catheter 38 has a proximal portion 64 having a second proximal shaft section 66 with the second shaft section 66 having a distal end 68 and a proximal end 70. The second shaft section 66 has a second drainage lumen 72 extending therethrough. The proximal portion 64 has a hollow connector 74 defining a continuation of the second drainage lumen 72. The proximal portion 64 has a side arm 76 having a valve 78 at a proximal end of the side arm 76, with the valve 78 being of known type which actuates by contact of a tip of a syringe. The proximal portion 64 has a second inflation lumen 80 extending through the side arm 76 from the valve 78 and through the second shaft section 66 to the distal end 68 of the second shaft section 66.

With reference to FIGS. 6-8, the catheter 38 has means for releasably locking 82 the first shaft section 40 to the proximal portion 64 while establishing communication between the first and second drainage lumens 46 and 72 and between the first and second inflation lumens 48 and 80. The locking means 82 comprises, a rigid body member 84 having a first tubular section 86 extending through the body member 84 and having opposed ends 88 and 90 projecting from the body member 84. The opposed ends 88 and 90 of the first tubular section 86 are receivable in the first and second inflation lumens 48 and 80, respectively. The body member 84 has a second tubular section 92 extending through the body member 84 and having opposed ends 94 and 96 projecting from the body member 84. The opposed ends 94 and 96 of the second tubular section 92 are receivable in the first and second drainage lumens 46 and 72, respectively.

The locking means 82 also has means for gripping 98 an outer surface of the first and second shaft sections 40 and 66, while the gripping means 98 clamps the first and second shaft sections 40 and 66 against the opposed ends of the first and second tubular sections 86 and 92. The gripping means 98 comprises, a pair of opposed threaded ends 100 and 102 of reduced diameter of the body member 84. The gripping means 98 also comprises a pair of threaded annular nuts 104 and 106 received on the opposed ends 100 and 102, respectively, of the body member 84. As shown, the inner diameter of the threads on the nuts 104 and 106 are tapered outwardly toward an outer end of the nuts 104 and 106. Thus, when the nuts 104 and 106 are placed at an inner position on the ends 100 and 102, the first and second shaft sections 40 and 66 may be received on the opposed ends of the first and second tubular sections 86 and 92 beneath the nuts 104 and 106. When the nuts 104 and 106 are moved to an outer position relative to the body member 84, the nuts 104 and 106 grip and clamp the first and second tubular sections 40 and 66 against the opposed ends of the first and second tubular sections 86 and 92 in sealing engagement in order to lock the first and second shaft sections 40 and 66 in place beneath the nuts 104 and 106. The first and second shaft sections 40 and 66 may be released by moving the nuts 104 and 106 to an inner position relative to the body member 84, and the first and second shaft sections 40 and 66 may be pulled from the opposed ends of the tubular sections 86 and 92.

In use, the needle 10 is passed through the body of a patient under radiologic vision until the tip 12 of the needle 10 is located in the renal calyces C of the kidney K to obtain access to the kidney chamber. With the needle 10 in place, the guide wire 16 is passed through the needle 10, and the needle 10 is removed with the guide wire 16 in place to establish a path to the kidney. Next, a plurality of dilators are inserted over the guide wire 16 in order to increase the size of the path to the kidney K, and the dilators are then removed.

With the first and second shaft sections 40 and 66 secured together by the locking means 82, the stylet 22 is inserted through the first and second drainage lumens 48 and 72 until the distal end 26 of the stylet 22 engages against the tip 58. Next, the guide wire 16 is passed through the tip opening 60 and through the stylet 22, and the catheter 38 is passed over the guide wire 16 until a distal portion of the catheter 38 is located in the renal calyces C. During this time, the stylet 22 supplies rigidity to the catheter 38 in order to facilitate the insertion procedure. The inflation valve 78 is then contacted by a tip of a syringe, and fluid is pumped through the first and second inflation lumens 48 and 80 and the first tubular section 86 in order to inflate the sleeve 50 in the renal calyces C. The stylet 22 is then removed from the catheter 38, the connector 74 is connected to an upstream end of a drainage tube which leads to a drainage bag, and urine drains through the catheter 38 and drainage tube to the bag for retention therein.

The scope 32 is utilized in the event that the physician desires to view the inside of the kidney K. In this event, the nuts 104 and 106 of the gripping means 98 are moved to the inner position in order to release the first and second shaft sections 40 and 66, such that the proximal portion 64 may be removed from the first shaft section 40. Next, the sheath 34 of the scope 32 is passed over the first shaft section 40, and the catheter 38 is removed through the sheath 34. During this time, the catheter 38 facilitates the placement procedure of the sheath 34 since it is unnecessary to redefine the tract to the kidney K. The optic telescope 36 is then inserted through sheath 34 in order to view the inside of the kidney K.

When examination of the kidney K has been completed, the telescope 36 is removed from the sheath 34, and the catheter first shaft section 40 is inserted through the sheath 34. The sheath 34 is then removed over the first shaft section 40, and the proximal portion 64 of the catheter 38 is locked to the first shaft section 40 through use of the locking means 82 and nuts 104 and 106, as previously described, after which the sleeve 50 is again inflated in the renal calyces C.

The foregoing detailed description is given for clearness of understanding only, and no unnecessary limitations should be understood therefrom, as modifications will be obvious to those skilled in the art.

I claim:

1. A catheter, comprising:

a first distal shaft section having a first distal drainage lumen extending therethrough, and a first inflation lumen extending through a wall of the first shaft section;

an elastic sleeve bonded to a distal portion of the first shaft section in circumferential zones defining a cavity beneath the sleeve communicating with the first inflation lumen;

a proximal portion comprising a second proximal shaft section having a second drainage lumen extending therethrough, a hollow connector defining a continuation of the second drainage lumen, a side arm having a valve, and a second inflation lumen extending through the side arm from the valve and through the second shaft section to a distal end of the proximal portion; and means for releasably locking the first shaft section to the proximal portion while establishing communication between the first and second drainage lumens and between the first and second inflation lumens, wherein the locking means comprises, a body member having a first tubular section extending through the body member and having opposed ends projecting from the body member, said opposed ends of the first tubular section being receivable in the first and second inflation lumens, a second tubular section extending through the body member and having opposed ends projecting from the body member, said opposed ends of the second tubular section being receivable in the first and second drainage lumens, and means for gripping an outer surface of the first and second shaft sections.

2. The catheter of claim 1 wherein the gripping means comprises means for clamping the first and second shaft sections against the opposed ends of the first and second tubular sections.

3. The catheter of claim 2 wherein the gripping means comprises, opposed threaded ends of the body member, and a pair of threaded annular nuts received on the opposed ends of the body member, with the inner diameter of the threads on the nuts being tapered outwardly toward an outer end of the nuts.

* * * * *